United States Patent [19]

Guha

[11] Patent Number: 5,488,075

[45] Date of Patent: Jan. 30, 1996

[54] CONTRACEPTIVE FOR USE BY A MALE

[76] Inventor: Sujoy K. Guha, 9 West Avenue, I.I.T., New Delhi 110016, Ind.

[21] Appl. No.: 309,135

[22] Filed: Sep. 20, 1994

[51] Int. Cl.⁶ .......................... C08L 25/08; C08K 5/41; A61K 31/74
[52] U.S. Cl. .................. 522/168; 522/79; 514/841; 514/708; 514/772.6; 424/78.33; 424/78.26; 424/78.20; 424/78.21; 424/DIG. 14
[58] Field of Search ................. 522/168, 79; 424/78.20, 424/78.21, 78.27, 78.33, DIG. 14; 514/841

[56] References Cited

U.S. PATENT DOCUMENTS

| | | | |
|---|---|---|---|
| 2,384,085 | 4/1941 | Gerhart | 522/168 |
| 2,955,994 | 10/1960 | Guthrie et al. | 522/168 |
| 3,398,226 | 8/1968 | Yamamoto et al. | 424/78.21 |
| 3,616,229 | 9/1968 | Wildi et al. | 424/78.21 |
| 4,432,967 | 2/1984 | Szymanski | 424/78 |
| 4,439,441 | 3/1984 | Hallesy et al. | 424/DIG. 14 |
| 4,760,097 | 7/1988 | Wiebe | 514/841 |
| 4,917,901 | 4/1990 | Bourbon et al. | 514/841 |

Primary Examiner—Marion E. Mc Camish
Attorney, Agent, or Firm—Helfgott & Karas

[57] ABSTRACT

The present invention relates to a contraceptive for use by a male. The contraceptive consists of a copolymer of styrene maleic anhydride which is prepared by the step of irradiation at a dose of 0.2 to 0.24 megarad for every 40 gms. of the copolymer. The contraceptive consists of an injectable fluid of said copolymer and pure dimethyl sulphoxide.

7 Claims, 1 Drawing Sheet

CONTRACEPTIVE FOR USE BY A MALE

This invention relates to a contraceptive and to a method of preparing the same. In particular, this invention relates to a contraceptive for use by a male.

BACKGROUND OF THE INVENTION

It is generally known that vas deferens is a suitable site for contraceptive intervention in the male. Vasectomy is a well established method of male contraception. In such a method, the vas deferens is cut and tied so as to prevent the sperms from flowing in the forward direction, and the sperms accumulate in the epididymes. Due to the presence of such sperms, the body generates enhanced antibodies to destroy the accumulated sperms. A disadvantage associated with such a method is that even after rejoining of the vas deferens, fertility is low as the body maintains the high level of antibodies and continues to destroy the sperms. Yet another disadvantage is that such a method requires surgery.

Besides vasectomy, reversible occlusion methods are also known in the art, which also prevents a forward flow of the sperm. One such occlusion method consists in implantating a reversible occlusion device for providing a blockage of the flow of sperms in the vas deferens. The device has a regulator knob outside of the vas deferens but inside the serotum. The regulator knob is normally operated by only a trained medical assistant. A disadvantage associated with such a device is that it also requires a surgery so as to allow an implantation. Another disadvantage is that during blockage, the body once again develops an enhanced level of antibodies to the sperms, which persists even upon opening or removal of the device. Yet another disadvantage arises in the instance where the closure may not be perfect resulting in a flow of sperms, though limited only quantitatively, but which cannot then be destroyed.

Yet another occlusion method known in the art consists in injecting polyurethane at a high pressure into the vas deferens. The polymer is further polymerized in the vas deferens by also introducing an initiator by which polyurethane sets into a solid plug to prevent a flow of the sperms in the forward direction. An additional disadvantage associated with such a method besides those described hereinabove with respect to the occlusion methods is that a back pressure is developed in the epididymes, which also reduces fertility.

Work by the present inventors on injecting styrene maleic anhydride in a solvent vehicle of dimethyl sulphoxide has been reported in Contraception 1993 : 48 October. Such a publication discloses in vitro pH-lowering effect but does not discuss the effect on the fertilizing ability of sperms.

SUMMARY OF THE INVENTION

In distinction the present invention relates to a contraceptive having a particular styrene maleic anhydride copolymer with DMSO provided in a particular manner to provide an effect on the fertilizing ability of sperm.

An object of this invention is to propose an improved contraceptive and a method of preparation for use in a non occlusive method of male contraception or occlusive only for a period of time.

Another object of this invention is to propose a contraceptive which no longer requires surgery.

Still another object of this invention is to propose a contraceptive which no longer requires the body to develop an enhanced level of antibodies to the sperms.

BRIEF DESCRIPTION OF THE DRAWINGS

Reference is now made to the accompanying drawings.

DETAILED DESCRIPTION OF THE INVENTION

Figure 1:
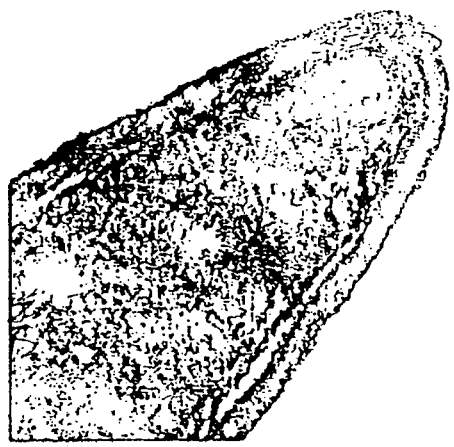
FIG. 1 shows a transmission electron micrograph of an untreated sperm head with intact acrosomal member.
Figure 2:
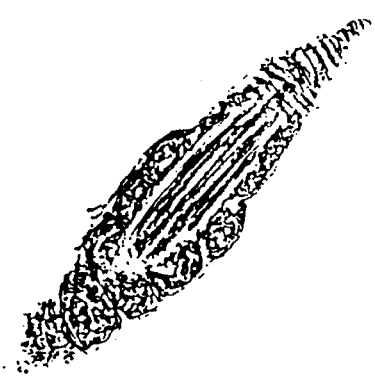
FIG. 2 shows a sperm head along with the tact treated with SMA and the acrosomal membrane partially damaged after 4 hours.
Figure 3:
FIG. 3 shows the sperm after 8 hours and where the membrane is fully damaged.

According to this invention there is provided a contraceptive for use by a male comprising an injectable fluid of a copolymer of styrene maleic anhydride in a solvent consisting of dimethylsulphoxide characterized in that said copolymer is prepared by the step of irradiation of the monomers at a dose of 0.2 to 0.24 megarad for every 40 gms. of copolymer.

In accordance with this invention the contraceptive comprises an injection consisting of a styrene maleic anhydride copolymer in a solvent vehicle of pure dimethylsulphoxide. Dimethylsulphoxide helps the penetration of polymer into the folds of the inner wall of the vas deferens and helps in retention of polymer. Further, the polymer remains in a localized region of the vas deferens and the tissue effects are limited to the vas deferens mucosa and does not extend to the muscle. The mucosa gets denuded.

In accordance with the present invention, the contraceptive is firstly injected only in the vas deferens by an incision in the scrotal skin or by a percutaneous method.

To inject a contraceptive into the vas deferens is known as such in the art. In the known art, the contraceptive consisted of passive polymers, which formed a plug or blockage to prevent a forward flow of the sperms. Thus, such polymers were not active compounds which could in any way effect the fertilizing ability of sperms.

In distinction, the contraceptive of the present invention comprises a solution of a polymer which is an active compound and affects fertilizing ability of sperms, and the acrosin and hyaluronidase enzymes.

The manner in which the contraceptive of the present invention works has still not been fully ascertained, except that in distinction to what has been disclosed in the aforesaid publication, just a lowering of the pH does not provide the necessary results and that other properties are required of the contraceptive. It is generally known that sperms as any other cell have a membrane. Thus one theory is that the introduction of the polymer solution produces a positive charge, and it is such a positive charge that disturbs the negative charge of the sperm membrane. The copolymer, when injected into the vas deferens, is an anhydride and hydrolizes in the presence of water molecules in the spermatic fluid. The polymer has a cyclic group which breaks upon hydrolysis and the anhydride is converted to a hydride. Due to such a conversion of the anhydride to hydride, the polymer develops a positive charge, which disturbs the negative charge of the sperm membrane. Thus, though the injection does function as an acidic material and that the pH is lowered, it has now been found that the polymer solution should develop a positive charge, when in contact with the spermatic fluid so as to disturb the negative charge of the sperm membrane. Thus, the contraceptive injection of the present invention is prepared in a manner and has a composition such that it hydrolizes in the presence of the spermatic fluid and develops a positive charge. Besides the formation of a positively charged contraceptive, it has been found that there is a lowering of the pH. It is not understood as to whether such a lowering of the pH is consequential to the positive charge or independent thereto, except that the contraceptive should be capable of developing positive charges.

As described hereinabove, the contraceptive of the present invention produces a positive charge. Other methods of producing such positive charges have been investigated and without lowering of pH. Thus, a plastic film as by way of example was electrostatically charged and dipped into the semen. Such investigations reflected that the sperms in the vicinity of the electrostatically charged film are affected, but due to the presence of water in the spermatic fluid, the charge gets lost. Thus, such investigations reflect, firstly, that the contraceptive should have properties such that the anhydride is converted to a hydride so as to provide positive charges to disturb the negatively charged membrane of the sperm. Secondly, such investigations reflect that the contraceptive should have properties such that the positive charges are bound to it and are not free flowing with the spermatic fluid. Thus, if lowering of the pH was a primary feature sought for from the contraceptive, which it has now been found not to be so, citric acid could have been injected into the vas deferens for lowering of the pH. However, the $H^+$ ions would then have a free flowing property.

It is believed that once the contraceptive is injected into the vas deferens, the polymer in an anhydrous state is converted into a hydride and the positive charge is bound thereto. Sperms having negative charge strike the positively charged polymer resulting in a membrane charge imbalance. Due to such an imbalance, it is believed that chloride ions are no longer kept out and extra amount of such ions with water flows through the membrane and, whereby, the head of the sperms swell up and ruptures the membrane. Inside the head, the sperm has, interalia, two enzymes, namely acrosin and hyaluromidase. Such enzymes leach out of the sperm head. Thus, the sperm is deficient of such enzymes which are required to penetrate the ovum.

Yet another theory is described herein. In clinical medicine, for example in neurosurgery and dermatology dimethyl sulphoxide (DMSO) is used. However, it has now been found that the form of DMSO used in these applications will not serve the purpose of the injectable contraceptive of the present invention for the male. For the contraceptive, it has now strangely been found that highly pure form ( spectroscopic grade) of DMSO is required. The sulphur (S) moiety of this form of DMSO is highly reactive. When styrene maleic anhydride (SMA) is mixed with this particular form of DMSO the sulphur moiety of DMSO interacts with the etheric oxygen (—o—) of the maleic anhydride moiety of the SMA thereby leading to the formation of an intermediate unstable complex of SMA and DMSO. The carbonyl oxygen of SMA being resonance stabilised, is not affected. The contraceptive is injected into the vas deferens in this complex form and not merely as a polymer dissolved in a solvent. In contradistinction the SMA could have been mixed in the usual medical grade of DMSO and such complexes would not exist in the required form and the resulting material will be ineffective for the present purpose.

When the SMA-DMSO complex of the form described hereinabove is injected into the vas deferens it comes under the influence of the proteins in the spermatic fluid in the vas deferens. The proteins are themselves complexes of amino acids. Some of the amino acids have an electrical charge distribution such that they are non polar. There are others with electrical charge distribution of a nature giving them a polar character. The polar amino acids react with the SMA-DMSO complex. Due to the formation of the SMA-DMSO complex, there is a chemical instability which enables the polar amino acids to detach the DMSO from the SMA while retaining the broken .bond and consequent polyelectrolyte structure of the SMA. Thus, the COOH of the maleic anhydride exists as $COO^- + H^+$. The reactions with the proteins take some time (approximately 48 hours) to complete. During this period the DMSO helps in the entry of the SMA into the folds of the vas deferens inner wall which promotes anchorage and retention of the contraceptive. When the reaction is complete, all the DMSO is detached and gets absorbed into the surrounding tissue and the blood stream for ultimate excretion. The net quantity of DMSO in a treatment dose is so small that even with the most sensitive analysis techniques currently available the pathways of excretion cannot be determined.

The place of DMSO is then taken over by the proteins of the spermatic fluid with the polar amino acids of the proteins linked to the SMA and sustaining the polyelectrolyte nature induced into the SMA. That is, the negative charge of $COO^-$ and the positive charge of $H^+$ are maintained in a bound state. The proteins form a layer around the SMA. An electrical charge double layer formation occurs with the proteins covering the SMA. The amino acids of proteins are Zwitterions having both electrically positive and electrically negative charged groups. In SMA the $COO^-$ are structurally larger than the $H^+$ but are less active. The more active $H^+$ ties up with the negative charged groups of the amino acids thus rendering them less effective in giving an external charge. Hence the positive charges of the amino acids are left to give an external influence. The protein-SMA agglomerate have then a positive charged surface which can influence the sperms. Also the protein layer over the SMA gives a potection to the SMA from dissolution. This phenomenon gives the long term action of the contraceptive in the vas deferens.

Besides having the active properties described hereinabove, the contraceptive of the present invention may also form a plug or blocking means for preventing the flow of the sperms. Thus, higher amounts or dose of the polymer may be injected into the subject, if so required by a clinician, and in which instance the contraceptive may function as a long term occlusive agent, or as an occlusive agent only for a period of time till the vas deferens lumen expands. The presence of such a higher dose allows the format ion of a plug or obstruct ion for flow of the sperms. However, the advantage of the contraceptive of the present invention is that it is reversible without requiring a surgery. Thus, if the copolymer is to be removed, the solvent is injected. The solvent for such a removal is sodium bicarbonate or DMSO. However, such sodium bicarbonate cannot be used for preparation of the contraceptive as it would then neutralize the positive charge.

In accordance with this invention, the injection comprises 40 to 60% weight by volume of the copolymer. If less than 40% of the copolymer is present then the contraceptive when injected into the vas deferens would have free flowing property.

If above 60%, then the material has a high viscosity whereby it becomes difficult to inject. By way of example and without implying any limitation thereto, styrene maleic anhydride is a copolymer of styrene and maleic anhydride in the ratio of 1.2:1 and preferably 1:1. The ratio of styrene and maleic anhydride present in the copolymer is important. Thus, and as by way of example, if the ratio of styrene to maleic anhydride in the copolymer is 2:1, then copolymer would function mainly as an occlusion device having a negligible positive charge and thus be associated with the disadvantages described hereinabove. Simultaneously, if the ratio of maleic anhydride to styrene in the copolymer is 1.5:1, the copolymer would have excessive charge with reduced stability and may have the possibility of being washed away. Further, and in such an instance, the muscle layer of the vas deferens would be affected due to the presence of a high charge.

The process of preparation of the copolymer comprises copolymerizing styrene and maleic anhydride monomer in ethyl acetate in a nitrogen atmosphere and subjected to a step of irradiation at a dose of 0.2 megarad for every 40 gms. of the polymer and a dose rate of 30 to 40 rad/Sec. Preferably the dose is 0.22 megarad and at a dose rate of 30 rad/Sec. The source of irradiation is cobalt 60 gamma radiation. The step of radiation is preferred to a chemical polymerization process. Further, a radiation polymerization provides a wider range of molecular weight distribution and thereby a combination of biological effects are achieved.

INFLUENCE OF RADIATION DOSAGE IN RESPECT OF THE CHARACTERISTICS OF THE INJECTABLE CONTRACEPTIVE FOR THE MALE.

|   | Radiation dose (Mrad) | Relative viscosity (with-respect to DMSO) |
|---|---|---|
| 1. | 0.1 | 1.0 |
| 2. | 0.15 | 1.2 |
| 3. | 0.2 | 1.3 |
| 4. | 0.22 | 1.5 |
| 5. | 0.23 | 1.8 |
| 6. | 0.24 | 2.2 |

The relative viscosity value is related to the molecular weight of the polymer. For proper injection and distribution in the vas deferens the relative viscosity required is in the range 1.5– 1.9. This corresponds to a molecular weight range of 60000–100.000.

After irradiation, the copolymer is precipitated by adding petroleum ether (60/80 grade) and then washed for removal of traces of monomers, homopolymers and maleic anhydride. The copolymer is dried and dissolved in 1,2 dichloro ethane for removal of styrene monomer. The polymer solution was filtered and filterate precipitated. The precipitated copolymer is washed, dried and stored.

Specifically, styrene maleic anhydride copolymer should have a molecular weight of 60,000 to 100,000 and preferably 90,000. If the molecular weight is lower than 60,000, the copolymer would then be less viscous and would tend to be eluted. Simultaneously, if the molecular weight is above 100,000, the copolymer would then function as a plug and would be difficult to wash out for reversal. Further, the hydrolized styrene maleic anhydride copolymer should have a pH of 4.0 to 4.5. The copolymer is dissolved in pure dimethyl sulphoxide as a solvent. DMSO is taken as a solvent as it has a high tissue penetration property, and therefore promotes entry on the copolymer in the folds of the inner lining of the vas deferens and thereby promotes anchorage DMSO and SMA is also an antimicrobial agent and thus inhibits any infection at the time of injection. DMSO gets absorbed and goes into the system.

Reference is made to the pH. Experiments were conducted on other buffer solutions using a low pH. Such buffer solutions of low pH produce substantial structural changes, namely the tails get curved and the head deformed. In SMA, though a lowering of pH is also achieved, the effect is more on the acrosomal membrane. Thus, for the same pH value of buffer using SMA, there is a difference.

In the instance where a fertility is not required for a certain period of time, then the dose of the contraceptive injected into the vas deferens is selected such that upon expiry of the non fertility period, the contraceptive itself has the free flowing property.

The relative viscosity of the contraceptive is 1.2 to 2.0, and preferably 1.5 to 1.9, relative to DMSO. If the viscosity is too low, there is then a possibility of the polymer flowing to the vermontenum, which is a sensitive member and the polymer can cause an irritation thereto. If the viscosity is too high, it would be difficult to inject the contraceptive and, further, the contraceptive would function exclusively as an occlusion device and does not allow the sperms to flow into the ejaculatory duct. As described hereinabove, one of the properties required of the contraceptive of the present invention is that it does not function permanently as an occlusion device, though it may function permanently as an occlusion if required by the clinicians or temporarily as an occlusion device till the vas deferens humen exponds.

Reference is now made to Table 1 which shows distribution of acrosome unreacted and acrosome reacted sperms in normal untreated subjects. The average fertile or unreacted sperms are 62% and the reacted or unfertile sperms are 35%.

TABLE 1

UNTREATED (CONTROL) SUBJECTS

| | Percentage of sperms in ejaculate | | | | | |
| --- | --- | --- | --- | --- | --- | --- |
| Subject | ACROSOME (Unreacted) | | | ACROSOME (Reacted) | | |
| Code | Dead | Live | Total | Dead | Live | Total |
| A | 12 | 39 | 51 | 32 | 16 | 48 |
| B | 26 | 40 | 66 | 19 | 15 | 34 |
| C | 20 | 49 | 69 | 17 | 14 | 31 |
| D | 20 | 43 | 63 | 16 | 11 | 27 |
| Average | | | 62 | | | 35 |

Reference is now made to Table 2 which shows the average fertile or unreacted sperms to have decreased 34% after SMA treatment and that the reacted or unfertile sperms increased to 65%.

TABLE 2

TREATED SUBJECTS

| | Percentage of sperms in ejaculate | | | | | |
| --- | --- | --- | --- | --- | --- | --- |
| Subject | ACROSOME (Unreacted) | | | ACROSOME (Reacted) | | |
| Code | Dead | Live | Total | Dead | Live | Total |
| E (DR) | 21 | 14 | 35 | 42 | 23 | 65 |
| F (SL) | 10 | 9 | 19 | 40 | 41 | 81 |
| G (ML) | 12 | 33 | 45 | 10 | 45 | 55 |
| H (CP) | 34 | 2 | 36 | 47 | 12 | 57 |
| Average | | | 34 | | | 65 |

Reference is now made to Table 3 which shows increased sperm enzyme release when the sperms are subjected to the influence of SMA.

TABLE 3

ENZYME RELEASE IN MILLIUNITS

| ENZYME/ NUMBER OF SPERMS | NORMAL | | | | TREATED WITH SMA |
|---|---|---|---|---|---|
| | 0 hrs. | ½ hrs. | 4 hrs. | 8 hrs. | 4 hrs. |
| ACROSIN | | | | | |
| $5 \times 10^6$ | 14.2 | 17.0 | 31.0 | 27.0 | 62.5 |
| ± | 2.5 | 2.7 | 1.2 | 5.5 | 7.8 |
| HYALURONIDASE | | | | | |
| $17.4 \times 10^6$ | 33.0 | 47.2 | 61.0 | 54.8 | 90.9 |
| ± | 4.5 | 12.3 | 4.4 | 6.5 | 6.6 |

Reference is made to an example for preparation of the copolymer. However, it is to be understood that such an example is not to construed in a limit manner and such as to restrict the scope of the invention.

EXAMPLE

Styrene and maleic anhydride monomers (1:1) ratio in ethyl acetate (monomer conc. 50% by wt.) is carried out in a nitrogen atmosphere in stoppered glass ampules. Samples are irradiated at a dose rate of 30 rad/sec. for a total dose of 0.24M rad at room temperature in a Co-60 gamma radiation chamber. After irradiation, copolymer is precipitated by adding petroleum ether and kept in 1,2-dichloroethane for 24 hr. changing the solvent three times with distilled water thoroughly and then immersed in water for 24 hrs. with repeatedly changing the water to remove the traces of monomers and homopolymers of maleic anhydride. The copolymer is dried and dissolved in dimethyl foramide (DMF). The polymer solution was filtered and filtrate was precipitated by adding petroleum ether (if it does not precipitate then precipitation can be done either by distilled water or normal saline). The precipitated copolymer is thoroughly washed with distilled water to remove the traces of solvent, dried and stored in a vacuum desicator over anhydrous calcium chloride.

Styrene maleic anhydride copolymer is stable at room temperature provided that it is maintained in a moisture free atmosphere. It is stored in tightly closed light resistant containers. No significant change occurs over a period of one year.

Styrene maleic anhydride copolymer in dimethyl sulphoxide is stored in glass container with stainless steel plungers for injection purposes. No air should remain within the container.

I claim:

1. A contraceptive for use by a male comprising an injectable fluid of a copolymer of styrene with maleic anhydride in a solvent consisting of dimethylsulphoxide characterized in that said copolymer is prepared by subjecting a mixture of styrene and maleic anhydride to the step of irradiation at a dose of 0.2 to 0.24 megarad for every 40 gms. of said mixture.

2. A contraceptive as claimed in claim 1 wherein said mixture of styrene and maleic anhydride is irradiated at a dose rate of 30 to 40 rads/sec.

3. A contraceptive as claimed in claim 1 wherein said copolymer has a molecular weight of 60,000 to 100,000.

4. A contraceptive as claimed in claims 1 to 3 wherein the viscosity is 1.2 to 2.0 relative to dimethylsulphoxide.

5. A contraceptive as claimed in claim 1 wherein said copolymer has styrene and maleic anhydride present in the ratio of 1.2:1 and preferably 1:1.

6. A contraceptive as claimed in claim 1 wherein the injected copolymer solution has a pH of 4.0 to 4.5.

7. A contraceptive as claimed in claim 1 wherein said copolymer has styrene and maleic anhydride present in the ratio of 1:1.

* * * * *